United States Patent
Ngo-Chu et al.

(10) Patent No.: US 10,736,784 B2
(45) Date of Patent: Aug. 11, 2020

(54) PATULOUS EUSTACHIAN TUBE STENT

(71) Applicant: Acclarent, Inc., Irvine, CA (US)

(72) Inventors: Don Q. Ngo-Chu, Irvine, CA (US);
Jetmir Palushi, Irvine, CA (US);
Ketan P. Muni, San Jose, CA (US)

(73) Assignee: Acclarent, Inc., Irvine, CA (US)

( * ) Notice: Subject to any disclaimer, the term of this patent is extended or adjusted under 35 U.S.C. 154(b) by 260 days.

(21) Appl. No.: 15/692,361

(22) Filed: Aug. 31, 2017

(65) Prior Publication Data

US 2019/0060125 A1 Feb. 28, 2019

(51) Int. Cl.
| | | |
|---|---|---|
| *A61F 11/00* | (2006.01) | |
| *A61F 2/88* | (2006.01) | |
| *A61B 17/12* | (2006.01) | |
| *A61F 2/915* | (2013.01) | |
| *A61B 17/00* | (2006.01) | |
| *A61F 2/958* | (2013.01) | |

(52) U.S. Cl.
CPC ...... *A61F 11/002* (2013.01); *A61B 17/12036* (2013.01); *A61B 17/12159* (2013.01); *A61B 17/12172* (2013.01); *A61F 2/88* (2013.01); *A61F 2/915* (2013.01); *A61F 11/008* (2013.01); *A61B 17/0057* (2013.01); *A61B 17/12022* (2013.01); *A61B 17/12099* (2013.01); *A61B 17/12177* (2013.01); *A61B 2017/00592* (2013.01); *A61B 2017/00787* (2013.01); *A61F 2/958* (2013.01); *A61F 2250/0039* (2013.01)

(58) Field of Classification Search
CPC .... A61F 2/915; A61F 2/88; A61F 2/82; A61F 2/86; A61F 2/89; A61F 2/90; A61F 2/91; A61F 11/002; A61B 2017/00787
See application file for complete search history.

(56) References Cited

U.S. PATENT DOCUMENTS

| | | | | |
|---|---|---|---|---|
| 5,192,307 | A | * 3/1993 | Wall | A61F 2/92 604/194 |
| 2003/0125792 | A1 | * 7/2003 | Braginsky | A61B 17/12 623/1.11 |
| 2010/0131044 | A1 | * 5/2010 | Patel | A61F 2/915 623/1.16 |
| 2010/0274188 | A1 | 10/2010 | Chang et al. | |
| 2010/0305697 | A1 | 12/2010 | Clifford et al. | |

(Continued)

FOREIGN PATENT DOCUMENTS

WO WO 2009/001358 A2 12/2008

OTHER PUBLICATIONS

European Search Report and Written Opinion dated Jan. 14, 2019 for Application No. 18191764.2, 6 pages.

*Primary Examiner* — Sarah A Simpson
(74) *Attorney, Agent, or Firm* — Frost Brown Todd LLC

(57) ABSTRACT

A system effectively narrows a patulous Eustachian tube (ET) of a patient with a guide catheter, instrument, and insert. The guide catheter includes a shaft, a lumen and a distal end configured to provide access the ET when the guide catheter is inserted into a head of the patient. The instrument comprises a shaft. The insert comprises a body configured to radially expand and retract between a non-expanded state and an expanded state. The insert is sized and shaped to be received within the first lumen when in the non-expanded state and is operable to expand to the expanded state to substantially reduce an effective diameter of the ET.

18 Claims, 14 Drawing Sheets

(56) References Cited

U.S. PATENT DOCUMENTS

| | | |
|---|---|---|
| 2013/0245749 A1* | 9/2013 | Sherry ............... A61F 2/07 |
| | | 623/1.36 |
| 2013/0274715 A1 | 10/2013 | Chan et al. |
| 2013/0338764 A1* | 12/2013 | Thornton ......... A61B 17/0401 |
| | | 623/2.11 |
| 2015/0202089 A1* | 7/2015 | Campbell ........... A61F 11/002 |
| | | 600/478 |
| 2015/0305943 A1 | 12/2015 | Hossainy et al. |
| 2015/0374963 A1 | 12/2015 | Chan et al. |
| 2017/0027724 A1 | 2/2017 | Hossainy et al. |

* cited by examiner

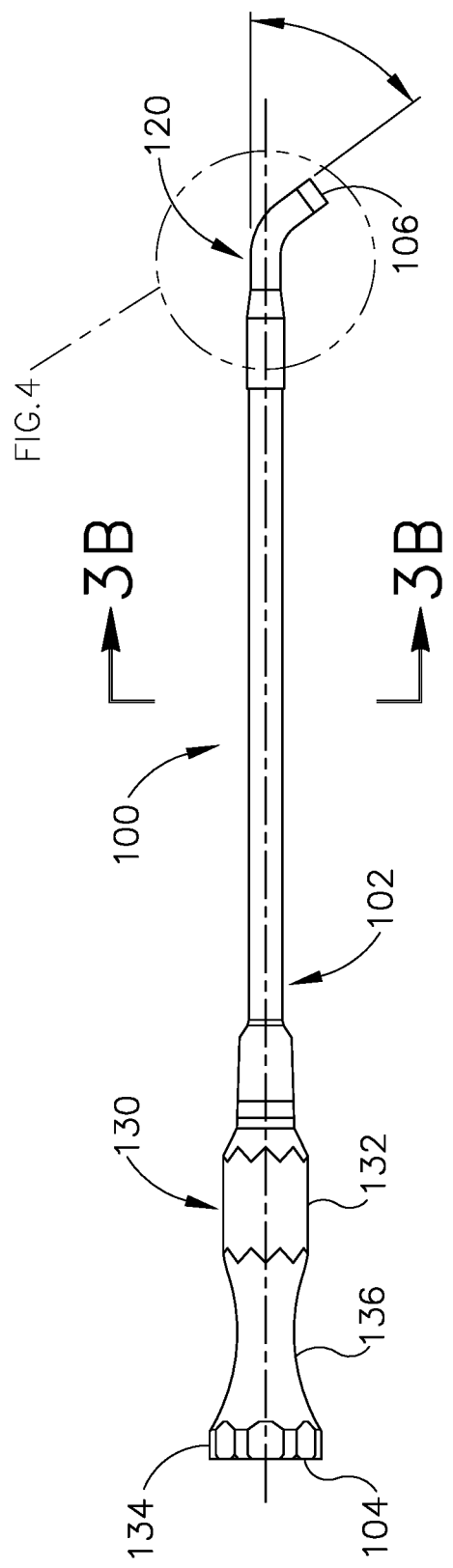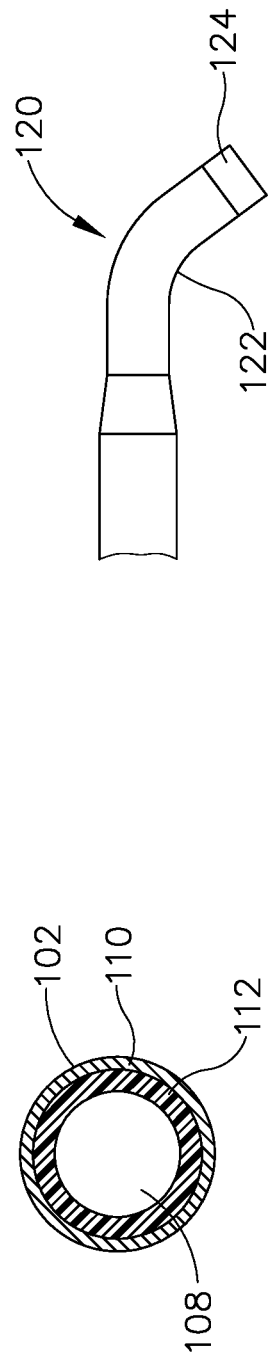

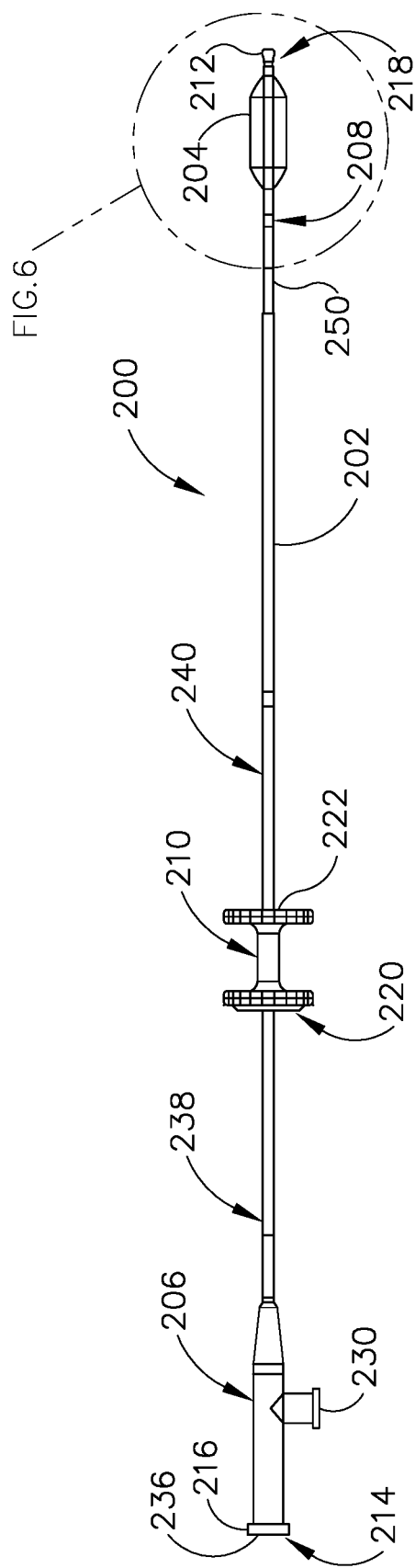
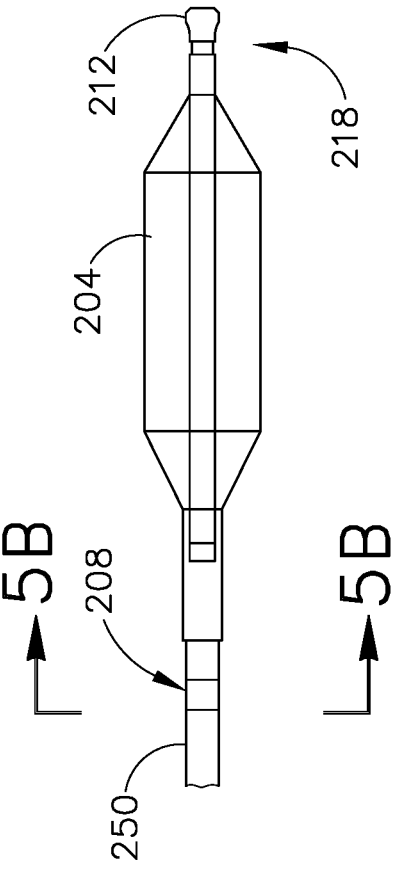
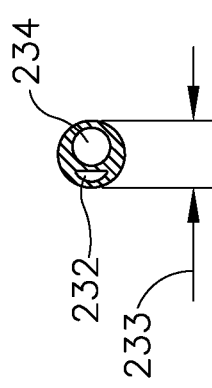
Fig.5A
Fig.5B
Fig.6

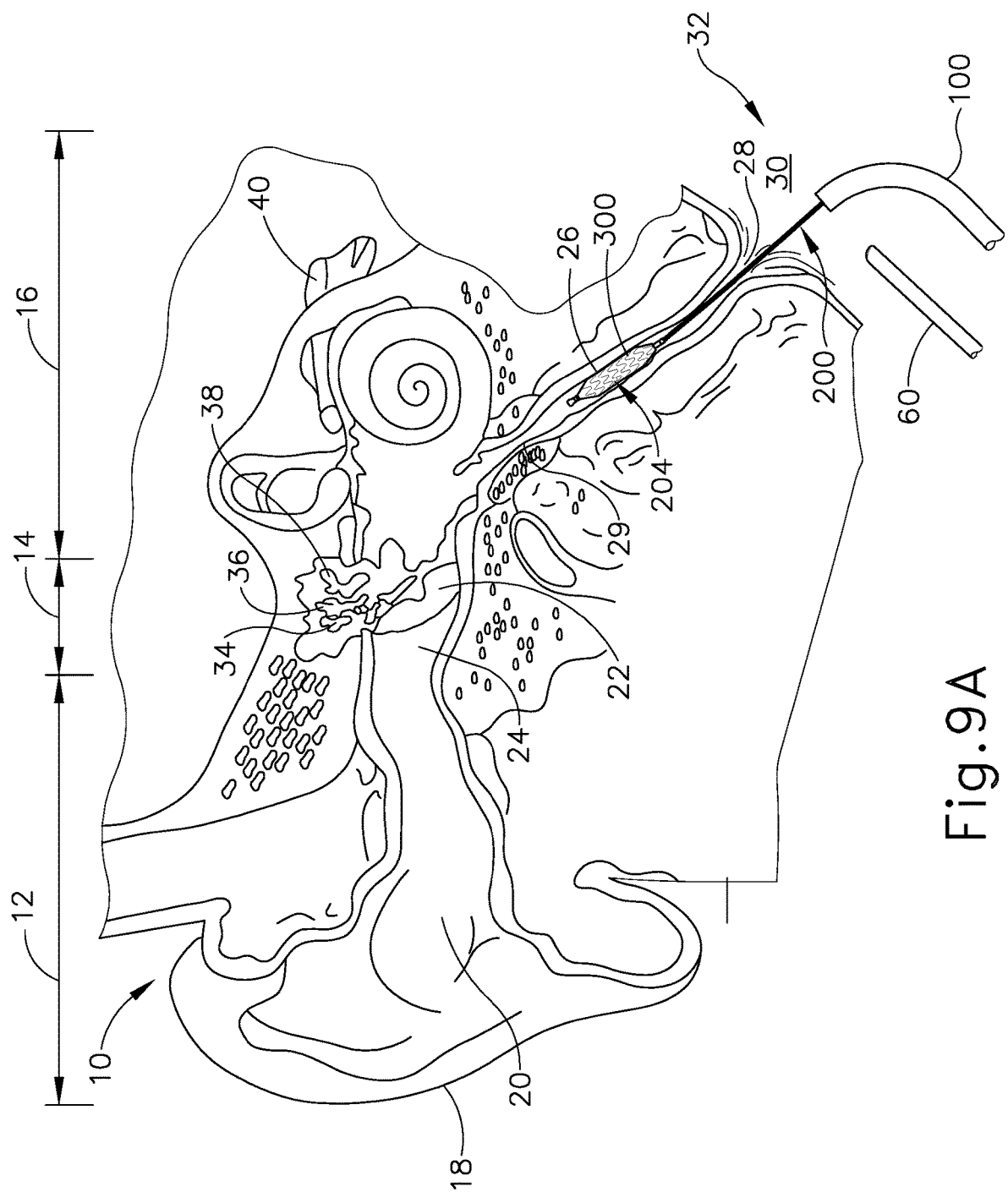

PATULOUS EUSTACHIAN TUBE STENT

BACKGROUND

Referring to FIGS. 1-2, the ear (10) is divided into three parts: an external ear (12), a middle ear (14) and an inner ear (16). The external ear (12) consists of an auricle (18) and ear canal (20) that gather sound and direct it toward a tympanic membrane (22) (also referred to as the eardrum) located at an inner end (24) of the ear canal (20). The middle ear (14) lies between the external and inner ears (12, 16) and is connected to the back of the throat by a Eustachian tube (ET) (26), which serves as a pressure equalizing valve between the ear (10) and the sinuses. The ET (26) terminates in a pharyngeal ostium (28) in the nasopharynx region (30) of the throat (32). In addition to the eardrum (22), the middle ear (14) also consists of three small ear bones (ossicles): the malleus (34) (hammer), incus (36) (anvil) and stapes (38) (stirrup). These bones (34, 36, 38) transmit sound vibrations to the inner ear (16) and thereby act as a transformer, converting sound vibrations in the canal (20) of the external ear (12) into fluid waves in the inner ear (16). These fluid waves stimulate several nerve endings (40) that, in turn, transmit sound energy to the brain where it is interpreted.

The ET (26) is a narrow, one-and-a-half inch long channel connecting the middle ear (14) with the nasopharynx (30), the upper throat area just above the palate, in back of the nose. The ET (26) functions as a pressure equalizing valve for the middle ear (14), which is normally filled with air. When functioning properly, the ET (26) opens for a fraction of a second periodically (about once every three minutes) in response to swallowing or yawning. In so doing, it allows air into the middle ear (14) to replace air that has been absorbed by the middle ear lining (mucous membrane) or to equalize pressure changes occurring on altitude changes. Anything that interferes with this periodic opening and closing of the ET (26) may result in hearing impairment or other ear symptoms.

Obstruction or blockage of the ET (26) results in a negative middle ear (14) pressure, with retraction (sucking in) of the eardrum (22). In adults, this is usually accompanied by some ear discomfort, a fullness or pressure feeling and may result in a mild hearing impairment and head noise (tinnitus). There may be no symptoms in children. If the obstruction is prolonged, fluid may be drawn from the mucous membrane of the middle ear (14), creating a condition referred to as serous otitis media (fluid in the middle ear). This may occur frequently in children in connection with an upper respiratory infection and account for hearing impairment associated with this condition.

When the ET (26) is blocked, the body may absorb the air from the middle ear (14), causing a vacuum to form that tends to pull the lining membrane and ear drum (22) inwardly, causing pain. Next, the body may replace the vacuum with more fluid which tends to relieve the pain, but the patient can experience a fullness sensation in the ear (10). Finally, the fluid can become infected, which can lead to pain, illness, and temporary hearing loss. If the inner ear (14) is affected, the patient may feel a spinning or turning sensation (vertigo).

Methods for treating the middle ear (14) and restriction or blockage of the ET (26) include those disclosed in U.S. Patent Pub. No. 2010/0274188, entitled "Method and System for Treating Target Tissue within the ET," published on Oct. 28, 2010, now abandoned, the disclosure of which is incorporated by reference herein; U.S. Patent Pub. No. 2013/0274715, entitled "Method and System for Eustachian Tube Dilation," published on Oct. 17, 2013, now abandoned, the disclosure of which is incorporated by reference herein; and U.S. Pub. No. 2015/0374963, entitled "Vent Cap for a Eustachian Tube Dilation System," published Dec. 31, 2015, issued as U.S. Pat. No. 10,350,396 on Jul. 16, 2019, the disclosure of which is incorporated by reference herein.

In some cases, rather than being restricted or blocked, the ET (26) may fail to close properly, or such that the ET (26) takes an inordinately prolonged amount of time to close after being opened, such that the ET (26) substantially remains in a patulous state. This may adversely affect a patient by causing variations in the upper airway pressure around the ET (26) and the middle ear (14). In some patients, a patulous ET (26) may create a feeling of dry sinus, an increased breathing rate with physical activity, higher than usual perceived volumes of sound, and/or other undesirable consequences. It may therefore be desirable to provide a form of treatment for a patulous ET (26). It may further be desirable for such a treatment to still provide some degree of ventilation and drainage for the ET (26), without completely closing the ET (26).

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 3A depicts a side elevational view of an exemplary guide catheter that may be used to position the dilation catheter of FIG. 5A;

FIG. 3B depicts a cross-sectional view of the guide catheter shown in FIG. 3A, taken along line 3B-3B of FIG. 3A;

FIG. 4 depicts an enlarged view of the distal end of the guide catheter shown in FIG. 3A;

FIG. 5A depicts a side elevational view of a balloon dilation catheter that may be used with the guide catheter of FIG. 3A;

FIG. 5B depicts a cross-sectional view of the balloon dilation catheter shown in FIG. 5A, taken along line 5B-5B of FIG. 6;

FIG. 6 depicts an enlarged view of the distal end of the balloon dilation catheter shown in FIG. 5A;

FIG. 9A depicts a cross-sectional view of the guide catheter of FIG. 3A and the balloon dilation catheter of FIG. 5A positioned in relation to the Eustachian tube of a patient, with the distal end of the balloon dilation catheter having the stent of FIG. 7 attached thereon, the stent being in the contracted state;

Figure 1:
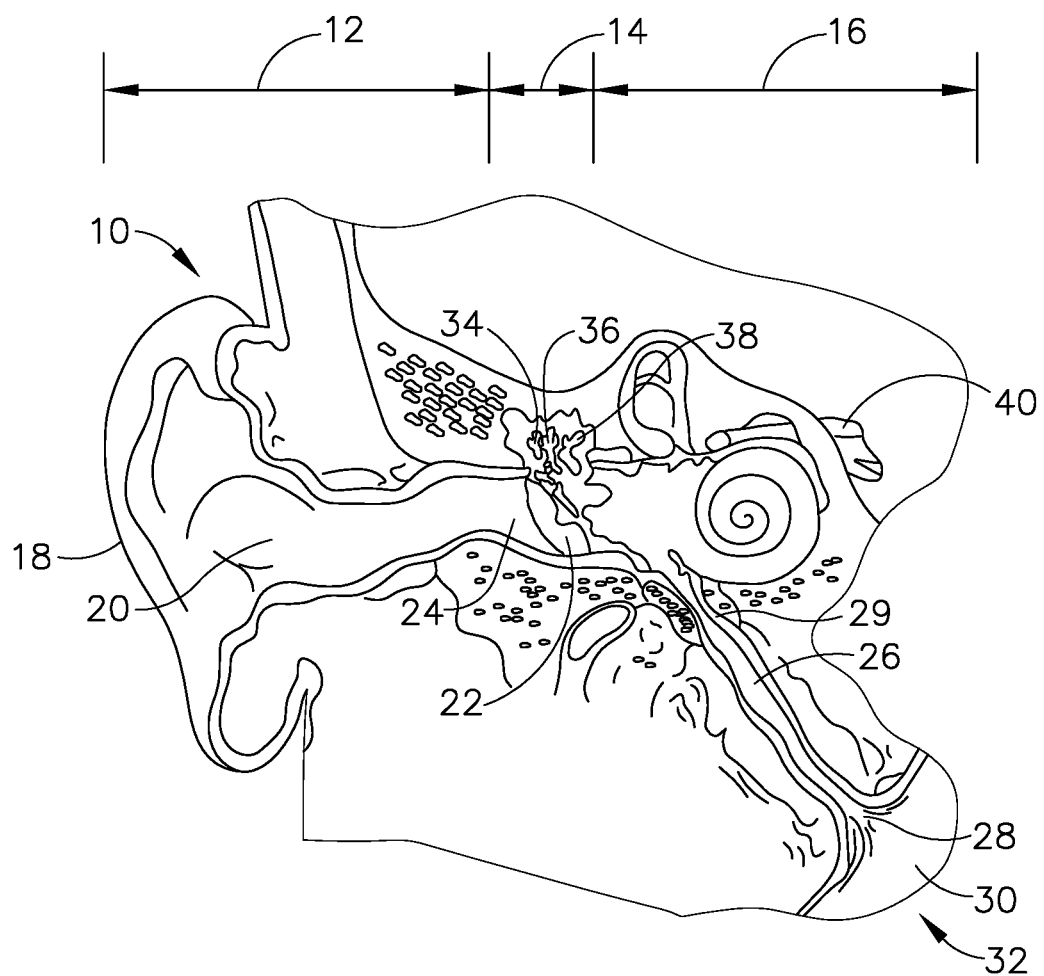
FIG. 1 depicts a cross-sectional view of a human ear showing the inner, middle and outer ear portions and the Eustachian tube connecting the middle ear with the nasopharynx region of the throat.
Figure 2:
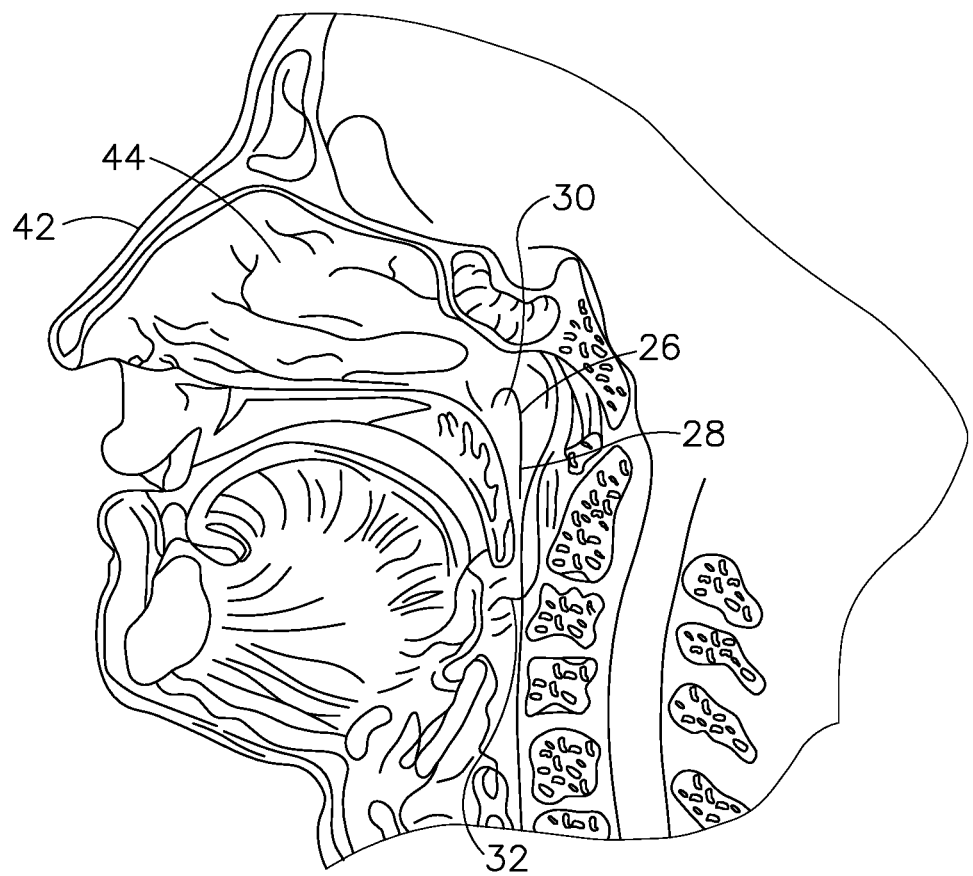
FIG. 2 depicts a cross-sectional view of a human head showing the nasopharynx region of the throat illustrated in FIG. 1 containing the pharyngeal ostium of the Eustachian tube illustrated in FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following detailed description should be read with reference to the drawings, in which like elements in different drawings are identically numbered. The drawings, which are not necessarily to scale, depict exemplary examples for the purpose of explanation only and are not intended to limit the scope of the invention. The detailed description illustrates by way of example, not by way of limitation, the principles of the invention. This description will clearly enable one skilled in the art to make and use the invention, and describes several examples, adaptations, variations, alternative and uses of the invention, including what is presently believed to be the best mode of carrying out the invention.

As used herein, the terms "about" and "approximately" for any numerical values or ranges indicate a suitable dimensional tolerance that allows the part or collection of components to function for its intended purpose as described herein.

I. Exemplary Eustachian Tube Catheter System

One example of a treatment that may be performed to treat an ET (26) that is in a patulous state for a prolonged period includes accessing and contacting the walls of the ET (26) with an implant that is deployed using a guide catheter (100) and a balloon dilation catheter (200), examples of which are shown in FIGS. 3A-6. Guide catheter (100) of the present example includes an elongate tubular shaft (102) that has a proximal end (104), a distal end (106) and a lumen (108) therebetween. The guide catheter (100) may have any suitable length, diameter, angle of bend, and location of the bend along the length of the catheter (100), to facilitate accessing an ET (26) opening, such as the pharyngeal ostium (28). In some examples, the guide catheter (100) may have a length between about 8 cm and about 20 cm, or more particularly between about 10 cm and about 15 cm, or more particularly about 11 cm.

FIG. 3B is a cross-sectional view of the elongate tubular shaft (102) of guide catheter (100). As can be seen, shaft (102) has an outer shaft tube (110), an inner shaft tube (112) and a lumen (108). The outer shaft tube (110) may be constructed of a stiff material such as stainless steel and the inner shaft tube (112) may be constructed of a more flexible material such as a polymeric material including but not limited to nylon and further including a PTFE liner. The lumen (108) has a diameter of between about 2 mm and 3 mm, preferably between about 2.5 mm and about 2.6 mm, such that the balloon dilation catheter (200) can be easily inserted into the lumen (108) for treating the ET (26). The combination of guide catheter (100) and balloon catheter (200) may a compact system that is designed for a one-handed procedure. By "compact," it is intended that the length of the guide catheter shaft that is distal of the bend in the guide catheter is between about 0.5 and 2.0 about cm, in some versions between about 1 and about 2 cm, and in some versions about 1 cm. The compactness may help reduce interference with other instruments, such as an endoscope (60) that may be used to help in visualizing the positioning of the system, as described below.

The distal portion (120) of guide catheter (100) is shown in an enlarged view in FIG. 4. The distal portion (120) of the guide catheter (100) may have a bend (122) with an angle between about 45 degrees and about 65 degrees, and more preferably between about 50 degrees and about 60 degrees, and particularly about 55 degrees, to facilitate access into the ET (26) via the pharyngeal ostium (28). The distal portion (120) of the guide catheter (100) is made of a transparent material such as a polymer including but not limited to nylon and PTFE such that balloon dilation catheter (200) is visible within the distal portion (120) and such that distal portion (120) is more flexible than the elongate shaft (102). The distal tip (124) of the distal portion (120) of the guide catheter (100) is made of PEBAX® (polyether block amide) such that it provides for atraumatic access to the ET (26), and may contain 20% barium sulfate or other similar radiopaque materials for visualizable access.

Referring again to FIG. 3A, the proximal portion (130) of guide catheter (100) includes a proximal hub (132) to aid in insertion of the balloon catheter into the ET (26). The hub (132) has a larger diameter proximal end (134) and a smaller diameter middle section (136) to facilitate stabilization of the guide catheter (100) in the nose, rotation of the guide catheter (100), and insertion of the balloon catheter (200) as will be described in further detail below. The hub (132) is ergonomically designed for insertion, location, and rotation through slight manipulations with one hand.

Balloon dilation catheter (200) of the present example is shown in FIG. 5A. The balloon dilation catheter (200) of the present example generally includes an elongate shaft (202) having a proximal end (214) and a distal end (218). The balloon dilation catheter (200) further includes a balloon (204) on the distal end (218) of the elongate shaft (202). The balloon (204) may be a polymer balloon (compliant, semi-compliant, or non-compliant). In some versions, the balloon (204) comprises a suitable non-compliant material such as but not limited to polyethylene terepthalate (PET), PEBAX® (polyether block amide), nylon or the like. The balloon catheter (200) may include any size of balloon including, but not limited to, balloons of 2 mm to 8 mm in diameter or of between about 5 mm and 6 mm (when inflated) and 12 mm to 24 mm in working length (for example 2 mm×12 mm, 3.5 mm×12 mm, 5 mm×16 mm, 5 mm×24 mm, 6 mm×16 mm, 6 mm×20 mm, 6 mm×24 mm, 7 mm×16 mm and 7 mm×24 mm) The balloon dilation catheter (200) generally includes a proximally located connection (230) for inflating/activating the balloon (204) by communicating a pressurized medium (e.g., saline) to balloon (204).

Figure 10A:
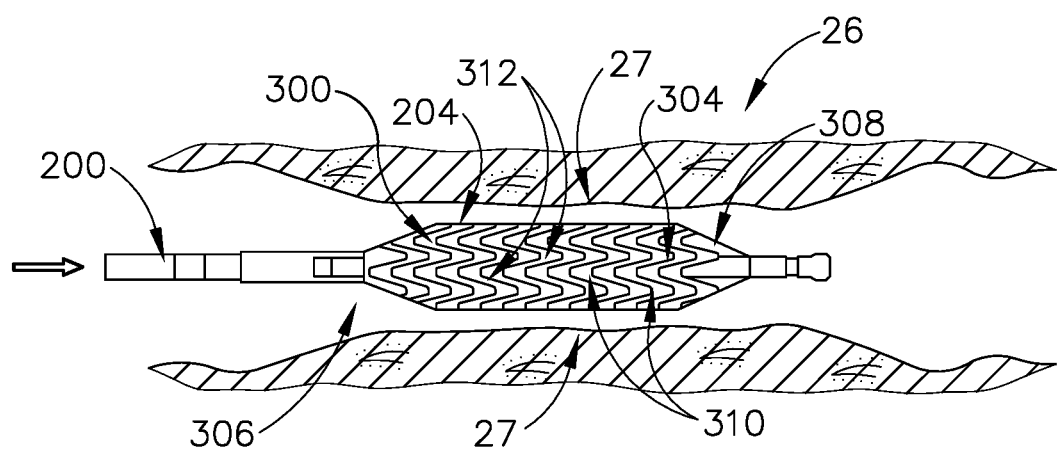
FIG. 10A depicts a cross-sectional side view of the balloon dilation catheter of FIG. 5A in the Eustachian tube of FIG. 9A, with the dilator in a deflated state to slidably position the stent of FIG. 7 within the Eustachian tube.
Figure 10B:
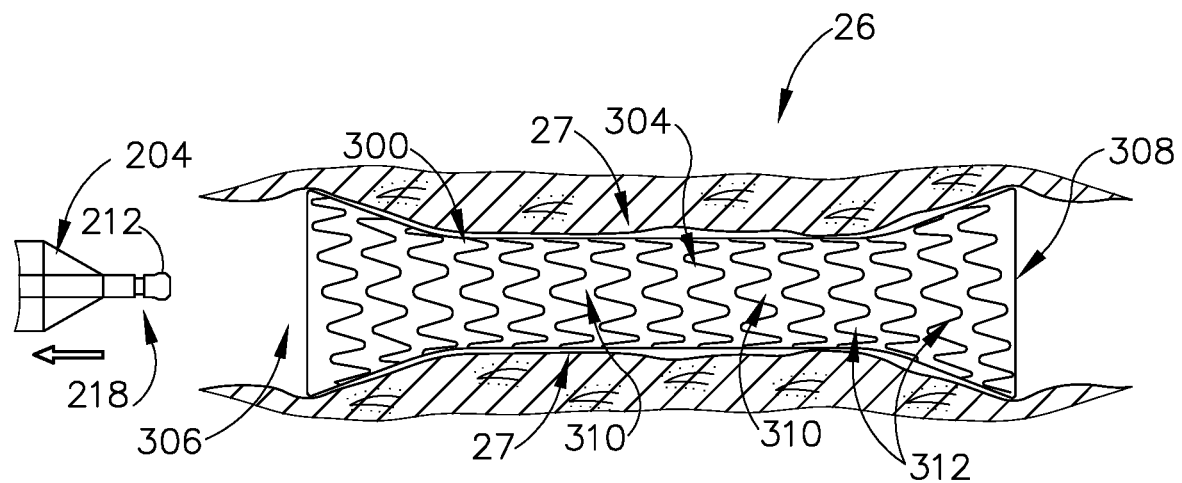
FIG. 10B depicts a cross-sectional side view of the balloon dilation catheter of FIG. 5A being withdrawn from the Eustachian tube of FIG. 9A, with the dilator being in a deflated state after having been expanded to an inflated state to secure the stent of FIG. 7 to the inner wall of the Eustachian tube.

Balloon (204) may be expanded to interact with an expandable stent (300) to treat the ET (26) after balloon (204) is placed in a desirable location in the ET (26), as shown in FIGS. 10A-10B and described in greater detail below. For example, the opening area of the ET (26) includes a pharyngeal ostium (28), and dilation catheter (200) may be advanced to position balloon (204) in the pharyngeal ostium (28). An endoscope (60) may be used to assist in positioning the dilation catheter (200). The endoscope (60) may be advanced through the nasal passage to view the dilation catheter (200). A marker (208) on a shaft of the dilation catheter (200) can be viewed from the endoscope (60) to approximate a location of the balloon (204) relative to the opening of the ET (26) (e.g., pharyngeal ostium (28)) based on a distance of the marker (208) from a proximal end of the balloon (204). Accordingly, dilation catheter (200) can be moved to place marker (208) in a desirable location before expansion of the balloon (204) in the ET (26).

Balloon dilation catheter (200) further includes an actuator (210). Actuator (210) has a proximal side 220 and a distal side (222). In the example shown in FIG. 5A, actuator (210) is secured by an adhesive to elongate shaft (202). The portion (240) of elongate shaft (202) that is distal of actuator (210) is sufficiently stiff to be guided through the nasal cavity and into the ET (26) and is constructed of stainless steel and may include a stainless steel hypotube. The portion (238) of elongate shaft (202) that is proximal of actuator (210) and the portion (250) that is distal to portion (240) is more flexible than the portion (240) and is constructed of a polymeric material including but not limited to PEBAX® (polyether block amide). In this way, proximal portion (238) of elongate shaft (202) will not interfere with the endoscope (60) described above as it is advanced through the nasal passage, such that the dilation catheter (200) can be easily viewed. The actuator (210) allows for easy, ergonomic one-handed advancement of dilation catheter (200) through guide catheter (100) and into the ET (26). Actuator (210) may be used to advance or retract in alternative ways including but not limited to use of the thumb, the index finger, or a combination of fingers (e.g., the index and middle fingers) or the thumb and the index or middle finger.

The distal end (218) of balloon catheter (200) further includes a tip (212) and a flexible shaft portion (250) that is constructed of a polymeric material including but not limited to PEBAX® (polyether block amide) that extends from the distal end of the elongate shaft (202) to the proximal end of balloon (204). In the example shown in FIG. 5A, tip (212) is a bulbous polymeric blueberry shaped, atraumatic tip and is about 1.5 mm to about 2 mm in length, with an outer diameter of between about 2 mm and about 3 mm. The smoothness and roundness of tip (212) facilitates advancement of the balloon catheter (200) by helping it glide smoothly through the ET (26). Tip (212) further acts as a safety stop. The isthmus (29) of the ET (26), shown in FIG. 1 is approximately 1 mm in diameter. The tip (212) diameter is larger than the outer diameter (233) of the elongate shaft (202) shown in cross-section in FIG. 5B such that the tip (212) size will prevent the balloon catheter (200) from passing through the isthmus (29) into the middle ear (14).

After balloon (204) is positioned within the ET (26) and inflated to an expanded state (e.g., as shown in FIG. 10B), balloon (204) may be held in location while in an expanded state for an extended period of time (e.g. several seconds or minutes). The balloon catheter (200) may also deliver a substance to the ET (26), such as one or more therapeutic or diagnostic agents. As described further below, balloon (204) may also carry an expandable stent (300) for delivery into the ET (26) upon expansion of balloon (204). Balloon dilation catheter (200) and guide catheter (100) may be removed from the patient after balloon (204) has been deflated/unexpanded, leaving stent (300) deployed in the ET (26). The ET (26) will resume functioning, normally opening and closing to equalize atmospheric pressure in the middle ear (14) and protect the middle ear (14) from unwanted pressure fluctuations and loud sounds.

II. Exemplary Method of Treating the Eustachian Tube

As noted above, some patients may have an ET (26) that remains patulous for a prolonged period, which may be undesirable for various reasons. It may therefore be desirable to insert a stent or other device into a patient's patulous ET (26), where the inserted stent or other device is capable of reducing the effective size of the ET (26) to thereby alleviate the negative effects created by the disorder. Providing a stent that has a narrow configuration but is able to expand outwardly to engage the inner walls of the ET (26) may be beneficial to avoid forcibly advancing an expanded rod into a patient's ET (26). In this instance, a stent is minimally invasive when initially inserted into the ET (26) but is subsequently expanded to fasten against the inner walls of the ET (26) to thereby pull the inner walls inwardly towards each other, forming a smaller diameter for the ET (26). By reducing the effective inner diameter of the ET (26), the patient may be alleviated of the various issues that are created when the ET (26) is in an abnormally enlarged state for a prolonged duration.

The following description provides various examples of devices that are configured to be deployed within the ET (26) to reduce the effective diameter of the ET (26). Ultimately, reducing the effective inner diameter of the ET (26) into a smaller profile for a prolonged period may be beneficial to minimize the likelihood that a patient will continue to experience the issues commonly associated with an ET (26) that maintains an abnormally large profile over a prolonged duration.

It should be understood that the stents and/or Eustachian tube plugs described below may be readily incorporated into any of the various guide members and dilation catheters described above and in any of the various surgical procedures described in the various references described herein. Other suitable ways in which the below-described stents and/or Eustachian tube plugs may be used will be apparent to those of ordinary skill in the art in view of the teachings herein.

A. Patulous Eustachian Tube Stent with Tissue Binding Coating

Figure 7:
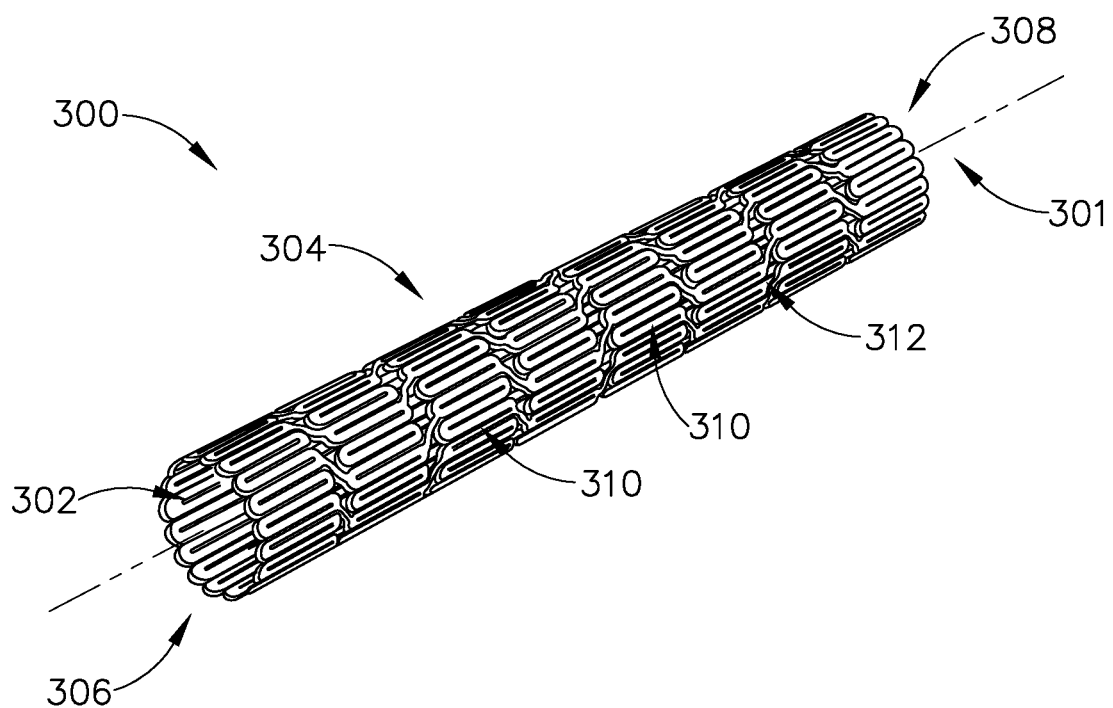
FIG. 7 depicts a perspective view of an exemplary stent in a contracted state.
Figure 8:
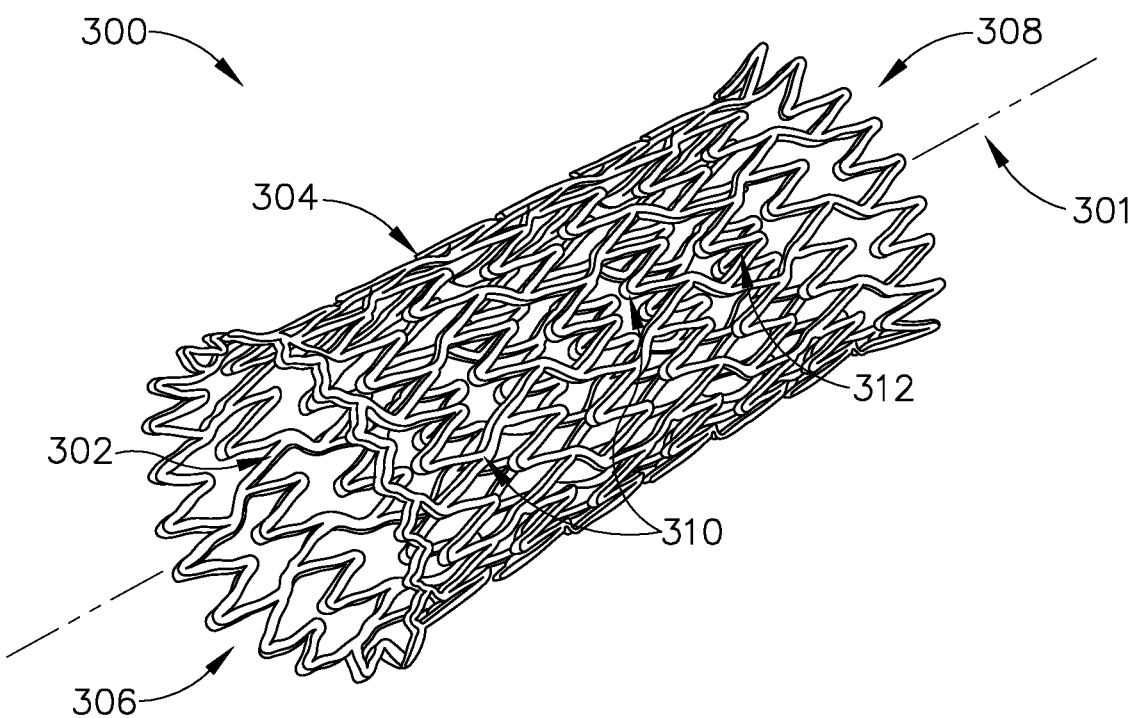
FIG. 8 depicts a perspective view of the stent of FIG. 7 in an expanded state.

FIGS. 7-8 show an exemplary stent (300) including an interior surface (302) and an exterior surface (304) extending between a proximal opening (306) and a distal opening (308). As will be described in greater detail below, openings (306, 308) are configured to provide access to interior surface (302) of stent (300) for an object, for example dilation catheter (200), to be received therein. Stent (300) is an elongate, cylindraceous device that is configured to be expandable about a longitudinal axis (301). As seen in FIG. 7, stent (300) is configured to naturally be in a contracted state by default such that stent (300) is resiliently biased to assume the contracted state upon the expansion of stent (300). Interior surface (302) and exterior surface (304) include a plurality of longitudinal struts (310) in a woven or looped arrangement such that each strut (310) of the plurality of struts (310) is immediately adjacent to another strut (310) thereby forming a mesh design or pattern. The mesh pattern of surfaces (302, 304) is configured to accommodate and allow for the expandability of stent (300). In other words, stent (300) is configured to be radially expandable from the selective separation and extension of the plurality of struts (310) along surfaces (302, 304), as seen in FIG. 8. In this instance, stent (300) is operable to be stretched to an expanded state upon the application of a predetermined outwardly directed force onto interior surface (302) and within stent (300).

Interior surface (302) and exterior surface (304) are configured to have a flexible configuration such that stent (300) is both expandable and easily maneuverable while in a contracted state for implantation within a patient's body, for example, in an ET (26). Surfaces (302, 304) of stent (300) may be formed of a metal bio-absorbable material. Moreover, surfaces (302, 304) may be coated with a biocompatible polymer coating. As merely an illustrative example, stent (300) may be formed of Resoloy®, a bioresorbable magnesium-alloy manufactured by MeKo Laster Material Processing, Hannover, Germany. Alternatively, for example, stent (300) may be formed of a biodegradable thermoplastic such as polylactic acid. In either instance, by being formed of a biocompatible material, stent (300) is configured to degrade within a patient's body after a predetermined degradation time. In other examples, stent (300) may be formed of a non-degradable material such that stent (300) is required to be manually removed; or such that stent (300) simply remains in the patient's body.

Stent (300) is further formed of a material that includes shape memory and/or elastic characteristics suitable for insertion into a patient's body. With the shape memory characteristics, stent (300) is resiliently biased to deform inwardly back to the default, contracted state (FIG. 7) after the selective expansion of surfaces (302, 304) to the expanded state (FIG. 8). In this instance, stent (300) has a resilient strength that is naturally inclined to transform back to an original contracted state up to a predetermined strength, such that stent (300) returns to the contracted state despite the presence of an intervening restraint or counter force applied thereon. As merely an illustrative example, stent (300) may be formed of an alloy such as Nitinol that includes shape memory and/or superelastic characteristics.

Stent (300) is further shaped and sized such to allow stent (300) to slidably advance into ET (26) when in the contracted state. For example, stent (300) may be sized between approximately 0.071 inches and approximately 0.124 inches (length) by approximately 0.0063 inches and approximately 0.0085 inches (width). Other various suitable dimensions will be apparent to those of ordinary skill in the art in view of the teachings herein.

Stent (300) further includes a tissue binding coating (312) along exterior surface (304). Tissue binding coating (312) is operable to fasten stent (300) against adjacent tissue upon the tissue contacting exterior surface (304). As such, stent (300) is configured to securely engage an adjacent tissue upon selectively abutting exterior surface (304) along the adjacent tissue. By way of example only, tissue binding coating (312) may comprise isocyanate, cyanoacrylate, and/or any other suitable biocompatible adhesive. Other suitable materials that may be used will be apparent to those of ordinary skill in the art in view of the teachings herein. Although not shown, it should be understood that other fastening means or mechanisms may be included along exterior surface (304) to thereby allow stent (300) to securely attach to an adjacent tissue. For example, stent (300) may include barbs or other mechanical anchoring features along exterior surface (304) that are configured to fasten stent (300) to ET (26).

In the present example, as seen in FIG. 9A, guide catheter (100), dilation catheter (200), and stent (300) are cooperatively used to treat the ET (26) under visual guidance using an endoscope (60). In use, guide catheter (100) may be advanced into a nostril and through a nasal cavity to position a distal end of catheter (100) at, in or near the pharyngeal ostium (28), which opens into the ET (26). In some variations, guide catheter (100) is advanced via the patient's mouth to reach the pharyngeal ostium (28). In either case, with the distal end of guide catheter (100) positioned at pharyngeal ostium (28), a guidewire (not shown) may be slidably advanced through dilation catheter (200), toward and into the ET (26). With the distal end of the guidewire extended into the ET (26), dilation catheter (200) and stent (300) are slidably advanced together along the guidewire into the ET (26) to a desired location for treatment. In particular, stent (300) is positioned on balloon (204) of dilation catheter (200) such that stent (300) advances unitarily with dilation catheter (200) into the ET (26). In other words, balloon (204) is positioned within interior surface (302) of stent (300). An adhesive and/or other feature(s) may be used to removably secure stent (300) to balloon (204). FIG. 10A shows dilation catheter (200) positioned such that balloon (204) and stent (300) are located in the ET (26), with balloon (204) in a non-expanded state, and with stent (300) in a contracted state.

In some instances, guide catheter (100), dilation catheter (200) and stent (300) may be passed through a nostril to the ET (26) on the ipsilateral (same side) of the head. In some other instances, guide catheter (100), dilation catheter (200) and stent (300) may be passed through a nostril to the ET (26) on the contralateral (opposite side) of the head. A guiding element such as an illuminating fiber may be used to aid in accessing the ET (26). A physician/user may place the index and middle fingers on either side of the smaller diameter middle section (136) of proximal hub (132) of guide catheter (100) and then place the thumb on the proximal side (220) of actuator (210), or within both sides of the actuator (210), and will use the thumb to slide the dilation catheter (200) through guide catheter (100) to position balloon (204) and stent (300) within the ET (26). Alternatively, the user may grasp proximal hub (132) of guide catheter (100) and use the index finger placed on the proximal side (220) of actuator (210) or in between the distal side (222) and the proximal side (220) of actuator (210) to advance dilation catheter (200) and stent (300).

The larger diameter tip (212) prevents balloon catheter (200) from advancing past the isthmus (29) and into the middle ear (14). Further, distal side (222) of actuator (210) will bottom out against proximal end (104) of guide catheter (100), such that the dilation catheter (200) cannot advance any further. The actuator (210) thus prevents the dilation catheter (200) from reaching past the isthmus (29) and reaching the middle ear (14). Further, actuator (210) can be positioned at the appropriate distance along the elongate shaft (202) such that access to the ET (26) may be from the contralateral or the ipsilateral side.

In an alternative example, dilation catheter (200) is advanced into a nostril of a patient without the use of a guidewire. As yet another alternative example, dilation catheter (200) may be advanced into a nostril of a patient without the use of a guide catheter (100). Balloon (204) of dilation catheter (200) may be placed directly within the ET (26), with stent (300) removably secured to balloon (204). The physician/user may advance dilation catheter (200) until the proximal side (220) of the actuator (210) is adjacent the patient's nostril. The distal side (222) of actuator (210) may bottom out against the patient's nostril, such that the dilation catheter (200) cannot advance any further. The actuator (210) prevents the catheter from passing the isthmus (29) and reaching the middle ear (14). Further, actuator (210) can be positioned at the appropriate distance along the elongate shaft (202) such that access to the ET (26) may be from the contralateral or the ipsilateral side.

Figure 9B:
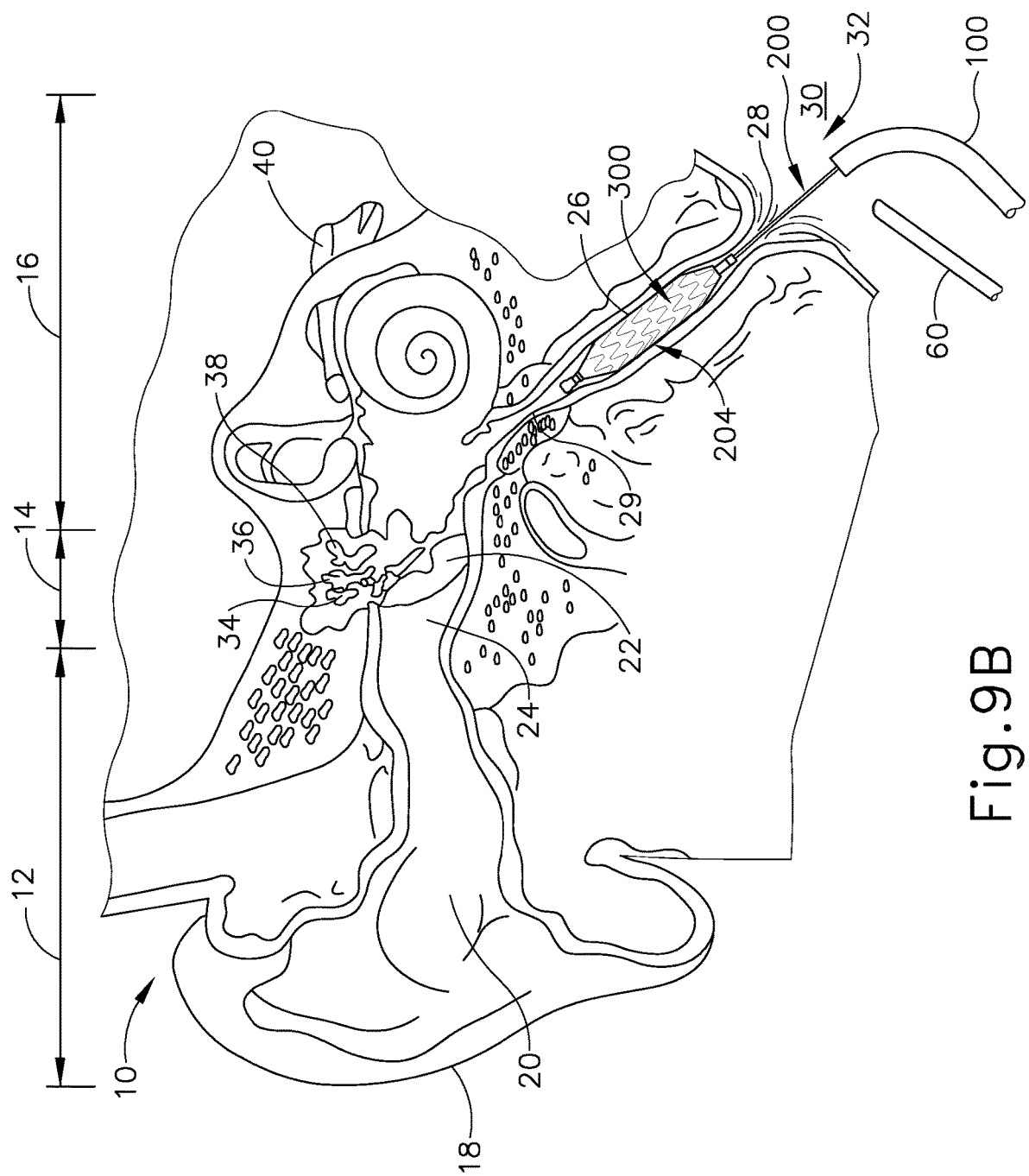
FIG. 9B depicts a cross-sectional view of the guide catheter of FIG. 3A and the balloon dilation catheter of FIG. 5A positioned in relation to the Eustachian tube of FIG. 9A, with the distal end of the balloon dilation catheter having the stent of FIG. 7 attached thereon, the stent being in the expanded state.

As best seen in FIG. 9B, with balloon (204) of dilation catheter (200) located within interior surface (302), fluid is communicated to balloon (204) to thereby inflate balloon (204) and expand stent (300) from the contracted state to the expanded state. The elongate shaft (202) contains adjacent dual lumen (232, 234) tubing (see FIG. 5B). By adjacent dual lumen tubing, it is intended that the lumens (232, 234) are next to each other but are spaced apart, one from the other. The inflation lumen (232) is used for inflation of the balloon (204) with water, contrast medium, or saline through inflation port (230) to a pressure of between about 3 and about 15 atmospheres, or of between about 6 and about 12 atmospheres. The injection lumen (234) permits the optional injection of water, medicament, or even the introduction of a guidewire through the injection port (236) at the proximal end (216) of the proximal connector (206).

In order to ensure that inflation port (230) is used for balloon (204) inflation only, inflation port (230) and injection port (236) may optionally have different type connectors. For example, inflation port (230) may be a female connector whereas injection port (236) is a male connector or vice versa. Alternatively, injection port (236) may have a right-handed thread connector and inflation port (230) may have a left-handed thread connector or vice versa.

Figure 11:
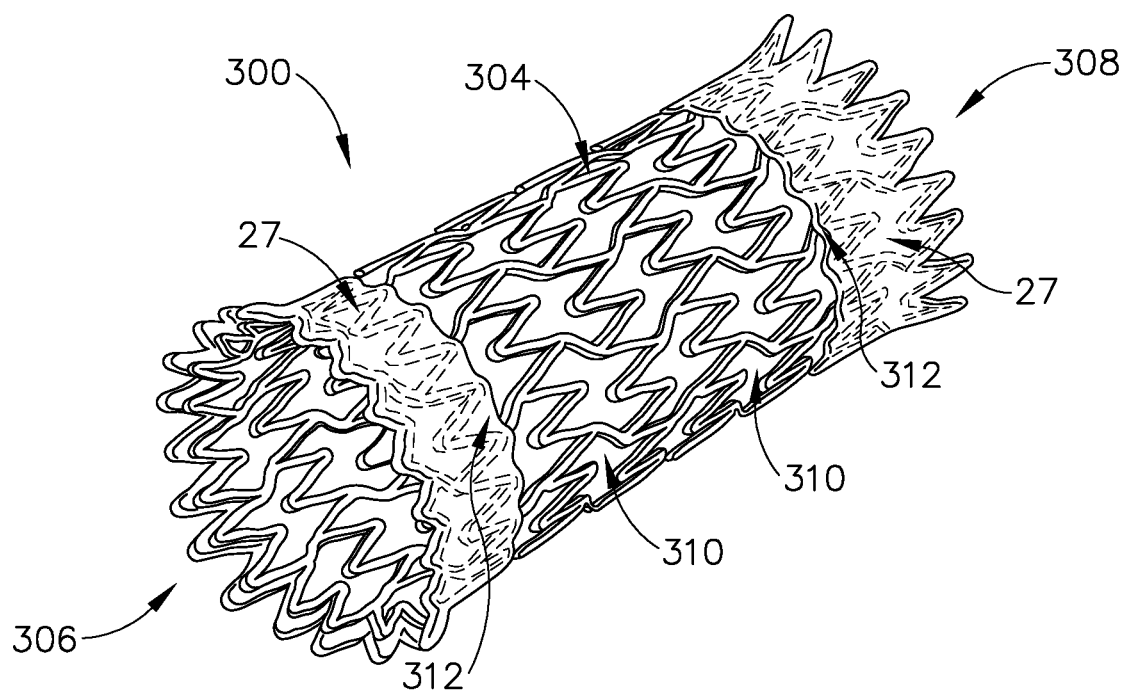
FIG. 11 depicts a perspective view of the stent of FIG. 7 in an expanded state fastened against the inner walls of the Eustachian tube.

As best seen in FIG. 10B, with stent (300) transitioned to the expanded state by the inflation of balloon (204), the plurality of struts (310) along surface (302, 304) are separated in a widened arrangement thereby resulting in exterior surface (304) contacting tissue sidewall (27) of the ET (26). As seen in FIG. 11, with exterior surface (304) abutting against tissue sidewall (27), stent (300) becomes securely fastened to tissue sidewall (27) due to the presence of tissue binding coating (312) along exterior surface (304) of stent (300). As such, stent (300) remains in the expanded state, securely fastened to tissue sidewall (27) of the ET (26), despite the withdrawal of balloon (204) from within stent (300).

Figure 10C:
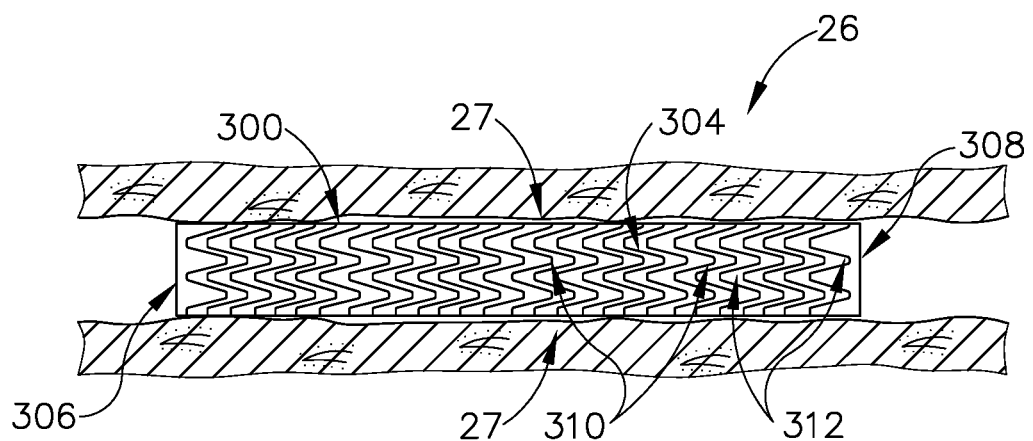
FIG. 10C depicts a cross-sectional side view of the Eustachian tube of FIG. 9A, with the balloon dilation catheter of FIG. 5A removed, and with the stent of FIG. 7 returned back to a contracted state thereby pulling the inner wall of the Eustachian tube inwardly.

With exterior surface (304) securely fastened to the ET (26) via tissue binding coating (312), stent (300) gradually retracts inwardly toward longitudinal axis (301) due to the absence of inflated balloon (204) positioned between interior surface (302), and due to the resilient bias of stent (300) urging stent (300) to return to the contracted state. As seen in FIG. 10C, the plurality of struts (310) along surfaces (302, 304) gradually return to an original position where stent (300) is transitioned back to the contracted state. In this instance, tissue sidewall (27) is simultaneously retracted inwardly, due to the coated-engagement with exterior surface (304), toward longitudinal axis (301) of stent (300). At this point, the abnormally enlarged diameter of ET (26) is effectively minimized to a predetermined diameter of surfaces (302, 304) in the contracted state. It should be understood the predetermined diameter of surfaces (302, 304) in the contracted state is determined in accordance with clinical data for normal sizes of an Eustachian Tube. Thus, the ET (26) is closed to a smaller profile for a predetermined period depending on the bio-absorption properties of stent (300).

It should be understood that, with stent (300) deployed in the ET (26), the ET (26) will be resiliently biased (by stent (300)) to assume a substantially closed state. Nevertheless, the properties of stent (300) may still allow ET (26) to open when the patient yawns or swallows, as would be expected in a normally operating ET (26), such that the ET (26) may still provide ventilation and drainage for the middle ear (14) even after stent (300) is deployed in the ET (26).

In versions where stent (300) is formed of a biodegradable or bioabsorbable material, stent (300) may be further configured to promote the growth of scar tissue within the ET (26). By way of example only, scar tissue growth may be promoted by one or more coatings on stent (300) and/or by one or more structural features of stent (300). In versions where stent (300) promotes the growth of scar tissue in the ET (26), the scar tissue may effectively maintain a reduced inner diameter in the ET (26), such that the scar tissue itself provides a long-term remedy to the otherwise patulous ET (26) after stent (300) has degraded or been absorbed.

B. Patulous Eustachian Tube Plug with Tissue Binding Coating

Figure 12:
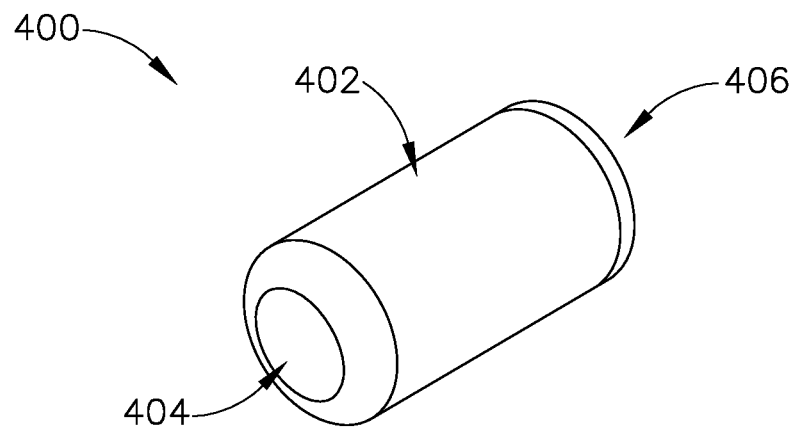
FIG. 12 depicts a perspective view of an exemplary Eustachian tube plug in an expanded state.
Figure 13:
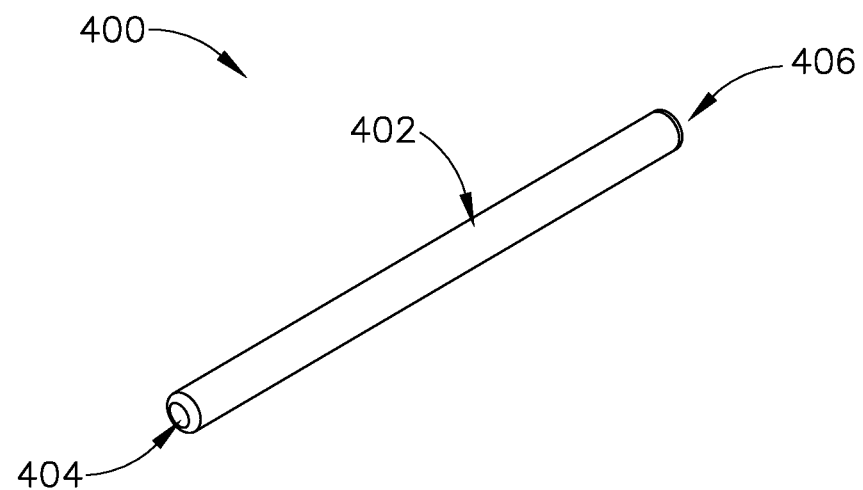
FIG. 13 depicts a perspective view of the Eustachian tube plug of FIG. 12 in a contracted state.

FIGS. 12-13 show an exemplary plug (400) including an elongated shaft (402) extending between a proximal end (404) and a distal end (406). Plug (400) is a longitudinal, cylindraceous device that is configured to be compressible. As seen in FIG. 12, plug (400) is configured to naturally be in an expanded or enlarged state by default. Plug (400) is formed of a silicone or other elastomeric material that has elastic properties allowing plug (400) to be compressible between the expanded state to a compressed state, as seen in FIG. 13. In other words, plug (400) is configured to be radially compressed and axially lengthened when compressed from the original expanded state (FIG. 12) to the compressed state (FIG. 13). In this instance, plug (400) is operable to be stretched or narrowed to a smaller profile when in a compressed state upon the application of a predetermined force onto the exterior surface of elongated shaft (402). By stretching plug (400) axially through the application of a force, plug (400) forms and maintains a smaller radial profile for as long as the force continues to be exerted onto the exterior surface of elongated shaft (402).

Although not shown, it should be understood that plug (400) may be oppositely configured such that plug (400) is naturally inclined to be in a narrow configuration or profile, as seen in FIG. 13. In this example, plug (400) is configured to be radially expanded and axially shortened when compressed along ends (404, 406) to thereby transition to the enlarged state shown in FIG. 12. Other various suitable arrangements or relationships of plug (400) will be apparent to those of ordinary skill in the art in view of the teachings herein.

Figure 14:
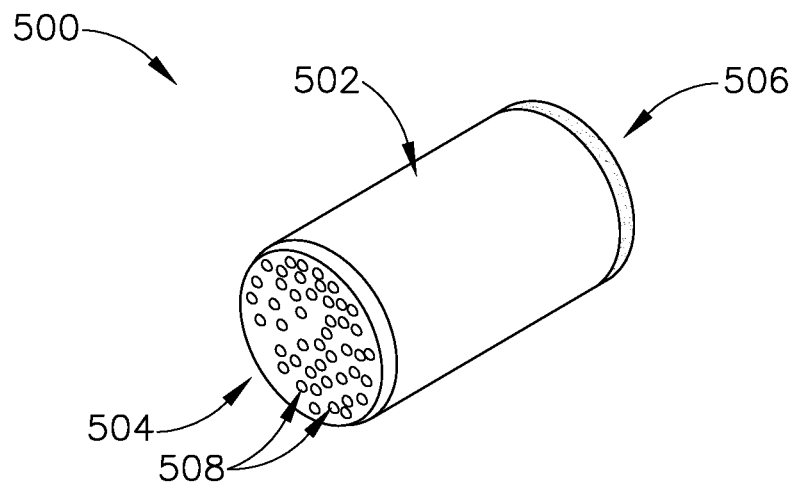
FIG. 14 depicts a perspective view of an exemplary alternative Eustachian tube plug including a plurality of pores along the proximal and distal ends, with the Eustachian tube plug in an expanded state.
Figure 15:
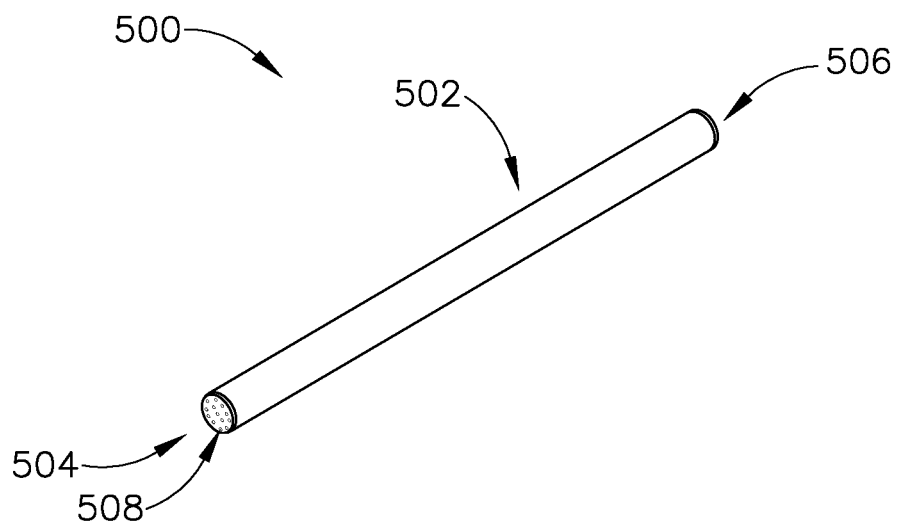
FIG. 15 depicts a perspective view of the Eustachian tube plug of FIG. 14 in a contracted state.

In some versions, an exemplary plug (500) may include a plurality of passageways (508) extending along the longitudinal length of plug (500) between a proximal end (504) and distal end (506), as seen in FIGS. 14-15. It should be understood that plug (500) of this example may be configured and operable just like plug (400) described above, except for the differences explicitly noted herein. Passageways (508) are configured to form a plurality of empty pockets along the longitudinal length of plug (500) to thereby allow plug (500) to have negative space contained therein. As best seen in FIG. 15, with the inclusion of passageways (508) within plug (500), plug (500) is configured to be compressed to an even smaller profile as the negative spaces created by passageways (508) are substantially reduced. In other words, passageways (508) provide additional ease in compressing plug (500).

In the present example, the ends of passageways (508) along proximal end (504) and distal end (506) are circular in shape. Although not shown, it should be understood passageways (508) may comprise various suitable shapes or profile as will be apparent to those of ordinary skill in the art in view of the teachings herein. As merely an illustrative example, passageways (508) may have a honeycomb shape. Passageways (508) are further configured to provide ventilation and drainage paths through plug (500) when positioned within the ET (26) to thereby enable fluid communication through plug (500).

In use, as similarly described above with respect to the installation of stent (300) within the ET (26), guide catheter (100) is advanced into a nostril and through a nasal cavity to position a distal end of catheter (100) at, in or near the pharyngeal ostium (28), which opens into the ET (26). With the distal end of guide catheter (100) positioned at pharyngeal ostium (28), a hollow sheath (480) is slidably advanced through guide catheter (100). Hollow sheath (480) comprises an internal channel (482) extending between a proximal opening (not shown) and a distal opening (484). Hollow sheath (480) has a push rod (490) and plug (400, 500) slidably disposed in internal channel (482) and contained therein. In particular, push rod (490) and plug (400, 500) are positioned in internal channel (482) such that distal end (406, 506) of plug (400, 500) is positioned adjacent to distal opening (484), with push rod (490) positioned at proximal end (404, 504) of plug (400, 500).

Figure 16A:
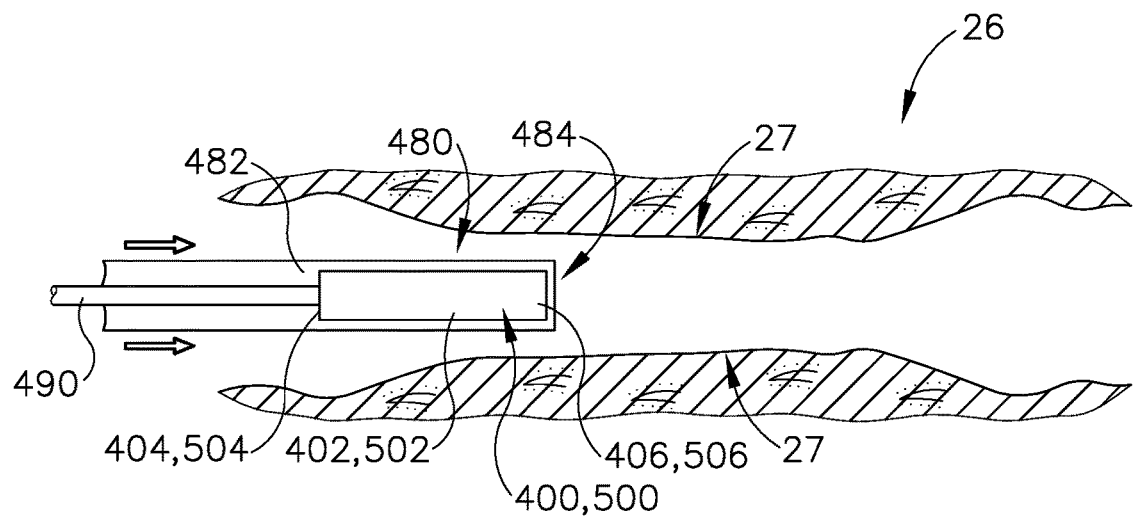
FIG. 16A depicts a cross-sectional side view of a Eustachian tube with a sheath slidably advanced therein, the sheath containing the Eustachian tube plug of FIG. 12 or FIG. 14 therein, with the Eustachian tube plug restricted to the contracted state by the dilation catheter.
Figure 16B:
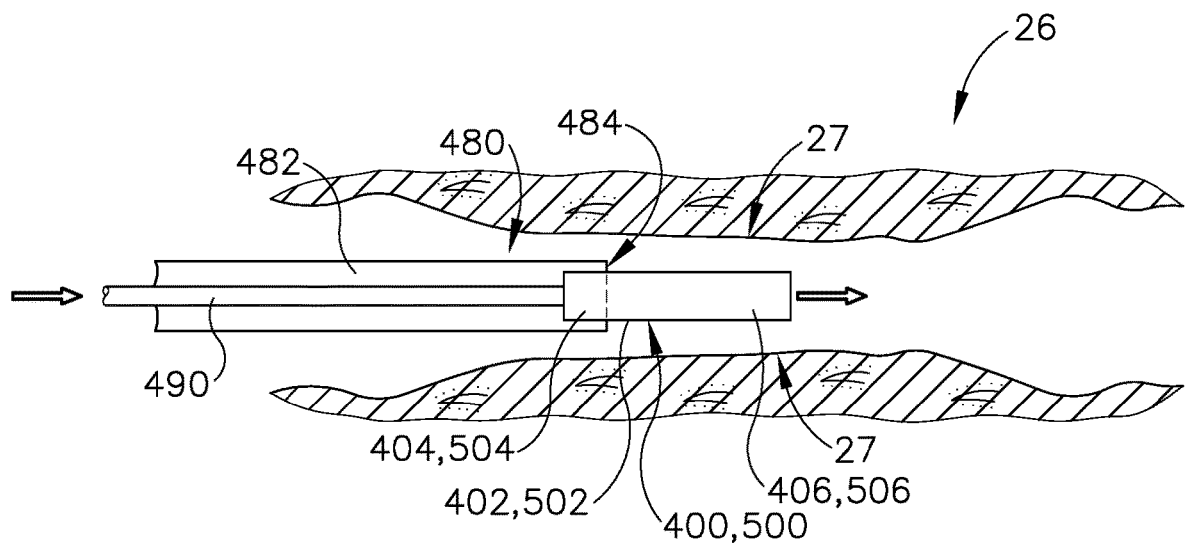
FIG. 16B depicts a cross-sectional side view of the Eustachian tube of FIG. 16A, with the Eustachian tube plug advanced distally from the sheath and with the Eustachian tube plug still in the contracted state.

With push rod (490) abutting against proximal end (404, 504) of plug (400, 500), push rod (490) ensures that plug (400, 500) does not proximally translate within internal channel (482) and away from distal opening (484). Internal channel (482) has a diameter that is smaller than a diameter of plug (400, 500) when plug (400, 500) is in the naturally expanded state, such that plug (400, 500) is compressed to the narrow state within internal channel (482), as seen in FIG. 16A. In other words, with plug (400, 500) positioned within internal channel (484), plug (400, 500) is restricted to and maintained in the compressed state due to the radial force exerted upon elongated shaft (402, 502) by the smaller profile of hollow sheath (480). Hollow sheath (480) is selectively advanced through the ET (26) until distal opening (484) is positioned proximate to a desired location for releasing plug (400, 500). As seen in FIG. 16B, push rod (490) is distally translated within internal channel (482) thereby encountering proximal end (404, 504) of plug (400, 500). Sheath (480) remains longitudinally stationary as push rod (490) is advanced distally relative to sheath (480). In this instance, plug (400, 500) is pushed out of internal channel (482) and through distal opening (484) until proximal end (404, 504) extends beyond distal opening (484).

Figure 16C:
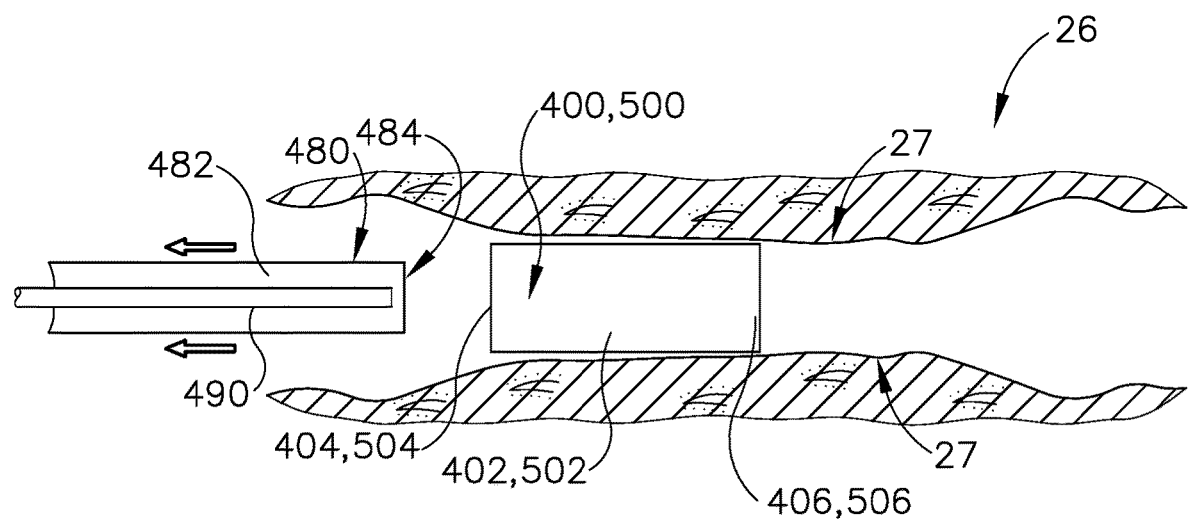
FIG. 16C depicts a cross-sectional side view of the Eustachian tube of FIG. 16A, with the Eustachian tube plug released from within the sheath and in an expanded state, the sheath being slidably retracted.

As seen in FIG. 16C, with plug (400, 500) extended distally beyond hollow sheath (480), plug (400, 500) resiliently expands to the original enlarged state. Plug (400, 500) is able to expand due to the absence of the radial force previously exerted onto exterior surface (402, 502) by hollow sheath (480). In this instance, elongated shaft (402, 502) continues to expand until encountering tissue sidewall (27) of the ET (26). With plug (400, 500) securely engaged against tissue sidewall (27) within the ET (26), the ET (26) effectively adopts a smaller profile in contrast to the abnormally large diameter of ET (26) without plug (400, 500) positioned therein. After plug (400, 500) is released from hollow sheath (480) at a desired position within the ET (26), hollow sheath (480) and push rod (490) are withdrawn from the ET (26) leaving plug (400, 500) in place within the ET (26). In instances where plug (500) is deployed, passageways (508) will provide ventilation and a drainage paths through plug (500) despite plug (500) being positioned within the ET (26). Even with such ventilation and drainage paths, plug (500) will still provide an effectively reduced diameter for the ET (26), thereby relieving the patient of the symptoms associated with a patulous ET (26).

Figure 17A:
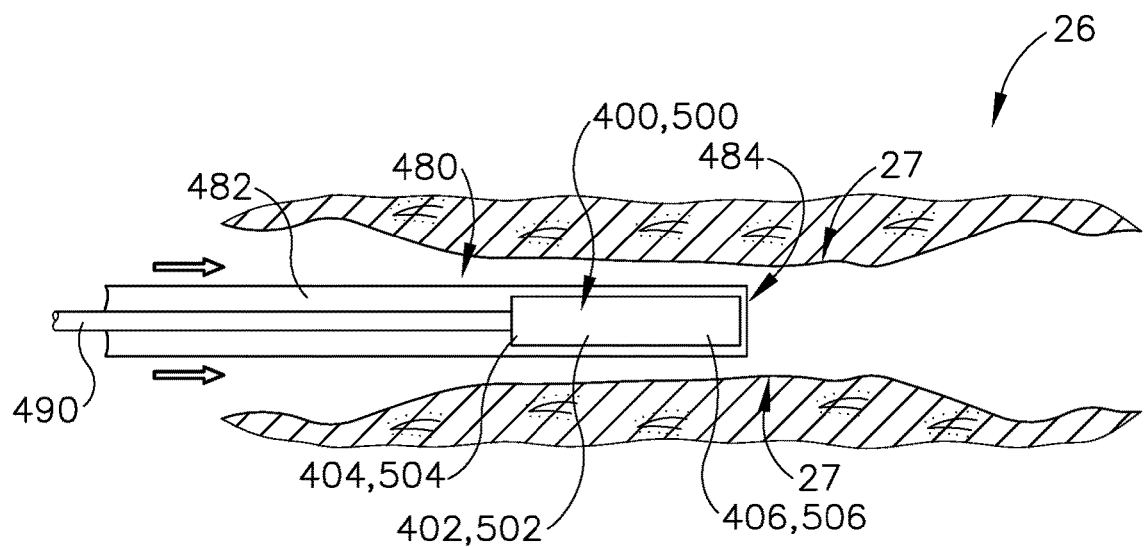
FIG. 17A depicts a cross-sectional view of a Eustachian tube with a sheath slidably advanced therein, the sheath containing the Eustachian tube plug of FIG. 12 or FIG. 14 therein, with the Eustachian tube plug restricted to the contracted state by the dilation catheter.
Figure 17B:
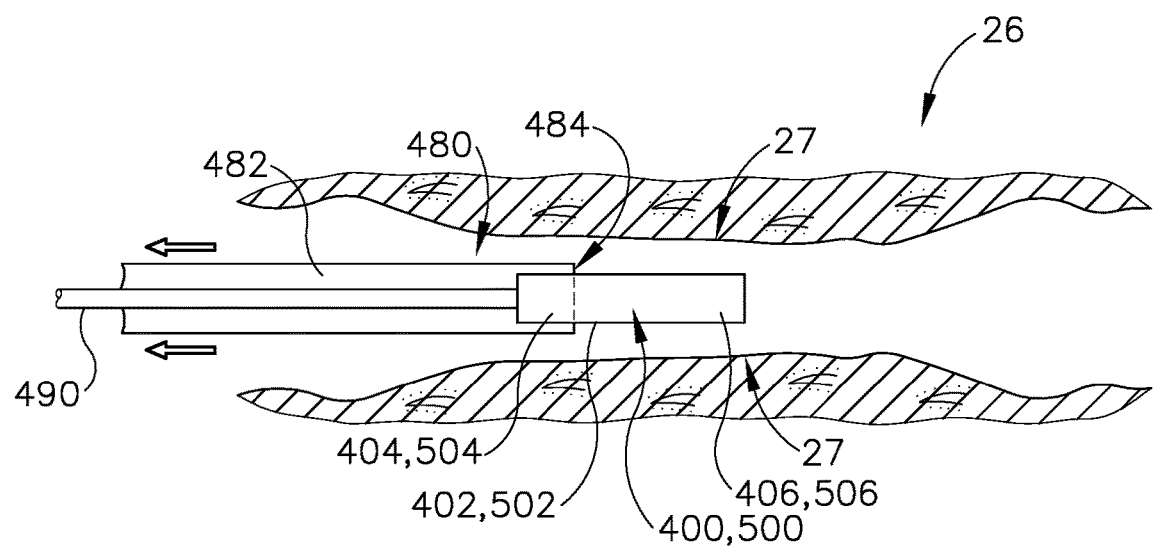
FIG. 17B depicts a cross-sectional view of the Eustachian tube of FIG. 17A, with the sheath slidably retracted and the Eustachian tube plug exposed from within the sheath.

Alternatively, in some applications, hollow sheath (480) is selectively advanced through the ET (26) until distal opening (484) is positioned at the desired location for plug (400, 500) to engage the ET (26), as seen in FIG. 17A. In this instance, in contrast to the prior method of positioning distal opening (484) proximate to the desired location where plug (400, 500) will be released from internal channel (482) as described above, distal opening (484) is selectively positioned at the location where plug (400, 500) is to engage the ET (26). In particular, as seen in FIG. 17B, hollow sheath (480) is extracted distally within the ET (26) while push rod (490) is steadily maintained in position, thus not being extracted distally with hollow sheath (480) despite being contained within internal channel (482).

Figure 17C:
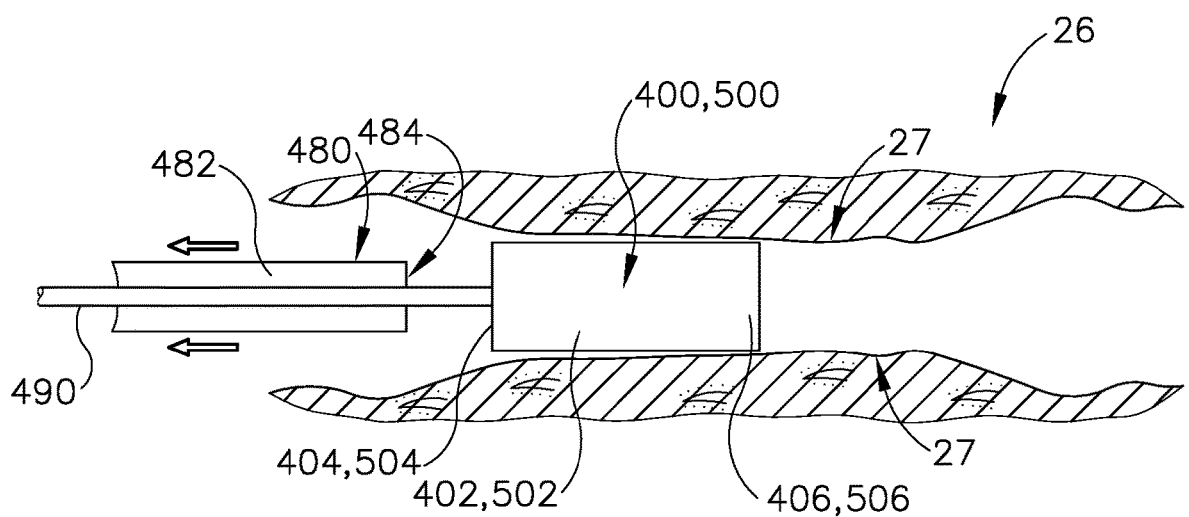
FIG. 17C depicts a cross-sectional view of the Eustachian tube of FIG. 17A, with the Eustachian tube plug released from within the sheath and in an expanded state, the sheath being slidably retracted.

In other words, as hollow sheath (480) is retracted from ET (26), push rod (490) is held in place in continued abutment with proximal end (404, 504) of plug (400, 500) such that distal end (406, 506) of plug (400, 500) beings to extend beyond distal opening (484). In this instance, plug (400, 500) is exposed from internal channel (482) as hollow sheath (480) is distally translated. FIG. 17C shows hollow sheath (480) substantially retracted from the ET (26) such that plug (400, 500) is no longer contained within internal channel (482), with a distal end of push rod (490) extending through distal opening (484) and maintaining plug (400) at the desired location through the engagement with proximal end (404, 504). With plug (400, 500) not contained within internal channel (482), plug (400, 500) resiliently expands to the original enlarged state. Plug (400, 500) radially expands due to the absence of a radial force that was previously applied to the exterior surface of elongated shaft (402, 502) through the confinement of internal channel (482).

As similarly described above, elongated shaft (402, 502) of plug (400, 500) expands radially until encountering tissue sidewall (27) of the ET (26). With plug (400) securely engaged against tissue sidewall (27) within the ET (26), ET (26) effectively adopts a smaller profile in contrast to the abnormally large diameter of ET (26) without plug (400, 500) positioned therein. After plug (400, 500) is exposed from within hollow sheath (480) at the desired location within the ET (26), hollow sheath (480) and push rod (490) are withdrawn from the ET (26) leaving plug (400, 500) in place within ET (26).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A system for providing a restriction in a patulous Eustachian tube (ET) of a patient, the system comprising: (a) a guide catheter comprising a shaft and a lumen extending therebetween, wherein the guide catheter further comprises a distal end configured to provide access to an opening in the ET when the guide catheter is inserted into a head of the patient; (b) an instrument comprising a shaft; and (c) an insert comprising a body configured to radially expand and retract between a non-expanded state and an expanded state, wherein the instrument is operable release the insert in the ET, wherein the insert is sized and shaped to be received within the lumen of the guide catheter when in the non-expanded state, wherein the insert is configured to reduce an effective diameter of the ET after transitioning from the expanded state to the non-expanded state in the ET or after transitioning from the non-expanded state to the expanded state in the ET.

Example 2

The system of Example 1, wherein the insert is resiliently biased to the non-expanded state.

Example 3

The system of Example 2, wherein the instrument further includes an expandable member, wherein the insert is configured to expand to the expanded state in response to a radially outward force applied to the body by the expandable member.

Example 4

The system of Example 3, wherein the insert is sized and configured to receive the expandable member when the insert is in the non-expanded state.

Example 5

The system of any one or more of Examples 3 through 4, wherein the insert is releasably secured to the expandable member.

Example 6

The system of any one or more of Examples 1 through 5, wherein the body comprises a plurality of longitudinal struts, wherein the struts are assembled in a looped arrangement such that each strut is adjacent to another strut thereby forming a mesh pattern.

Example 7

The system of any one or more of Examples 1 through 6, wherein the insert further comprises a fastening mechanism configured to securely attach the insert to the ET upon contact between the body and the ET.

Example 8

The system of Example 7, wherein the fastening mechanism is positioned along the body.

Example 9

The system of any one or more of Examples 7 through 8, wherein the fastening mechanism comprises a tissue binding coating along an outer surface of the body.

Example 10

The system of any one or more of Examples 1 through 9, wherein the insert is formed of a biodegradable material such that the insert is configured to dissolve after a predetermined duration within the ET.

Example 11

The system of any one or more of Examples 1 through 10, wherein the insert is formed of an elastic material operable to flexibly expand the body.

Example 12

The system of any one or more of Examples 1 or 6 through 11, wherein the insert is resiliently biased toward the expanded state, wherein the guide catheter is configured to constrain the insert in the non-expanded state.

Example 13

The system of Example 12, wherein the body is configured to contract longitudinally when radially expanded to the expanded state.

Example 14

The system of any one or more of Examples 12 through 13, wherein the insert includes a plurality of passageways extending within the body, wherein passageways are configured to enable fluid communication through the body.

Example 15

The system of any one or more of Examples 12 through 14, wherein the instrument further comprises a pusher operable to drive the insert out of the guide catheter in response to relative longitudinal movement between the guide catheter and the pusher.

Example 16

An apparatus for providing a restriction in a patulous Eustachian tube (ET) of a patient, the apparatus comprising: (a) a body, wherein the body is resiliently biased to radially expand from an elongated state to a widened state, wherein a longitudinal length of the body is configured to shorten when in the widened state such that the longitudinal length of the body is longer in the elongated state relative to the widened state, wherein the body is sized and configured to be inserted in an ET when the body is in the elongated state, wherein the body is sized and configured to bear against a sidewall of the ET when the body is in the widened state; (b) a plurality of passageways formed through the body; wherein the body in the elongated state is sized and configured to be received within an interior of a shaft; and wherein the body in the widened state is operable to provide restricted fluid communication through an ET through via the passageways.

Example 17

The apparatus of Example 16, wherein the body is formed of a biodegradable material such that the body is configured to dissolve after a predetermined duration within the ET.

Example 18

A method for providing a restriction in a patulous Eustachian tube (ET) of a patient using an insert, wherein the insert comprises a body configured to be expandable from a contracted state to an expanded state, the method comprising: (a) directing the insert into an oro-nasal cavity of the patient while the insert is in the contracted state; (b) advancing the insert into an opening of the ET; (c) further advancing the insert within the ET to a desired target site; (d) expanding the insert to the expanded state; and (e) restricting an effective diameter of the ET via the insert.

Example 19

The method of Example 18, wherein the insert is resiliently biased toward the contracted state, wherein the acts of directing, advancing, and further expanding are performed using an instrument having an expandable member, wherein the insert is carried by the expandable member, wherein the act of expanding the insert comprises expanding an expandable member to overcome the resilient bias of the insert, wherein the expanded insert is secured to the ET, wherein the act of restricting the effective diameter of the ET comprises contracting the expandable member, thereby allowing the insert to resiliently return to the contracted state.

Example 20

The method of Example 18, wherein the insert is resiliently biased toward the expanded state, wherein the acts of directing, advancing, and further expanding are performed using an instrument having an outer sheath and an inner rod, wherein the insert is carried within the outer sheath, wherein the act of expanding the insert comprises providing relative longitudinal movement between the outer sheath and the inner rod to thereby release the insert from the outer sheath, wherein the act of restricting the effective diameter of the ET is provided by the insert resiliently returning to the expanded state.

IV. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, examples, examples, etc. described herein may be combined with any one or more of the other teachings, expressions, examples, examples, etc. that are described herein. The above-described teachings, expressions, examples, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various examples of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, examples, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A system for providing a restriction in a patulous Eustachian tube (ET) of a patient, the system comprising:
   (a) a guide catheter comprising a shaft and a lumen extending therebetween, wherein the guide catheter further comprises a distal end configured to provide access to an opening in the ET when the guide catheter is inserted into a head of the patient;
   (b) an instrument comprising a shaft; and
   (c) an insert comprising a body configured to radially expand and retract between a non-expanded state and an expanded state, wherein the body comprises an outer surface with a tissue binding coating, wherein the instrument is operable to release the insert in the ET by driving the insert into the expanded state such that the outer surface and the tissue binding coating are configured to engage the ET, wherein the insert is sized and shaped to be received within the lumen of the guide catheter when in the non-expanded state, wherein the insert is resiliently biased toward the non-expanded state such that the insert is configured to reduce an effective diameter of the ET after being released into the ET by transitioning from the expanded state to the non-expanded state in the ET via the tissue binding coating.

2. The system of claim 1, wherein the instrument further includes an expandable member, wherein the insert is configured to expand to the expanded state in response to a radially outward force applied to the body by the expandable member.

3. The system of claim 2, wherein the insert is sized and configured to receive the expandable member when the insert is in the non-expanded state.

4. The system of claim 2, wherein the insert is releasably secured to the expandable member.

5. The system of claim 1, wherein the body comprises a plurality of longitudinal struts, wherein the struts are assembled in a looped arrangement such that each strut is adjacent to another strut thereby forming a mesh pattern.

6. The system of claim 1, wherein the insert is formed of a biodegradable material such that the insert is configured to dissolve after a predetermined duration within the ET.

7. The system of claim 1, wherein the insert is formed of an elastic material operable to flexibly expand the body.

8. The system of claim 1, wherein the body is configured to contract longitudinally when radially expanded to the expanded state.

9. A system for providing a restriction in a patulous Eustachian tube (ET) of a patient, the system comprising:
   (a) a guide catheter comprising a shaft and a lumen extending therebetween, wherein the guide catheter further comprises a distal end configured to provide access to an opening in the ET when the guide catheter is inserted into a head of the patient;
   (b) an instrument comprising a shaft; and
   (c) an insert comprising a body extending along an axis, wherein the body comprises an outer surface and a tissue binding coating attached to the outer surface, wherein the body is configured to radially expand and retract between a non-expanded state and an expanded state, wherein the body is sized and shaped to be received within the lumen of the guide catheter when in the non-expanded state, wherein the body is biased toward the axis, wherein the instrument is operable to drive the body into the expanded state such that the body is configured to attach to the ET via the tissue binding coating, wherein the body is configured to reduce an effective diameter of the ET by transitioning from the expanded state to the non-expanded state while the body is attached to the ET via the tissue binding coating.

10. The system of claim 9, wherein the instrument comprises a balloon configured to drive the body into the expanded state.

11. The system of claim 10, wherein the instrument comprises a bulbous tip.

12. The system of claim 9, wherein the shaft defines a first lumen configured to transmit fluid to the balloon.

13. The system of claim 12, wherein the shaft defines a second lumen configured to slidably receive a guidewire.

14. The system of claim 9, wherein the insert is formed from a metal material.

15. The system of claim 9, wherein the insert is formed from a biodegradable thermoplastic.

16. The system of claim 9, wherein the insert comprises an inner surface.

17. The system of claim 9, wherein the insert extends along a longitudinal axis.

18. A system for providing a restriction in a patulous Eustachian tube (ET) of a patient, the system comprising:
- (a) a guide catheter comprising a shaft and a lumen extending therebetween, wherein the guide catheter further comprises a distal end configured to provide access to an opening in the ET when the guide catheter is inserted into a head of the patient;
- (b) an instrument comprising a shaft; and
- (c) a stent extending along an axis, wherein the stent is configured to radially expand and retract toward and away from the axis, wherein the stent comprises an outer surface with a tissue binding coating, wherein the instrument is operable to drive the stent away from the axis such that the outer surface and the tissue binding coating are configured to engage the ET, wherein the stent is resiliently biased toward the axis such that the stent is configured to reduce an effective diameter of the ET after engaging the ET via the tissue binding coating.

* * * * *